US012594227B2

(12) United States Patent
Bell et al.

(10) Patent No.: US 12,594,227 B2
(45) Date of Patent: Apr. 7, 2026

(54) TETRAPEPTIDE AND COMPOSITIONS COMPRISING TETRAPEPTIDES

(71) Applicant: THE BOOTS COMPANY PLC, Nottingham (GB)

(72) Inventors: Michael David Bell, Alfreton (GB); Eleanor Jane Bradley, Beeston (GB); Yegor Doush, West Bridgford (GB); Michael John Sherratt, High Peak (GB); Matiss Ozols, Manchester (GB); Alexander Eckersley, Manchester (GB)

(73) Assignee: THE BOOTS COMPANY PLC, Nottingham (GB)

( * ) Notice: Subject to any disclaimer, the term of this patent is extended or adjusted under 35 U.S.C. 154(b) by 444 days.

(21) Appl. No.: 18/037,480

(22) PCT Filed: Nov. 16, 2021

(86) PCT No.: PCT/EP2021/025445

§ 371 (c)(1),
(2) Date: May 17, 2023

(87) PCT Pub. No.: WO2022/106057

PCT Pub. Date: May 27, 2022

(65) Prior Publication Data

US 2023/0414477 A1      Dec. 28, 2023

(30) Foreign Application Priority Data

Nov. 17, 2020    (EP) ..................................... 20020538

(51) Int. Cl.
*A61K 8/64*        (2006.01)
*A61Q 19/08*      (2006.01)
*C07K 5/11*        (2006.01)

(52) U.S. Cl.
CPC ................ *A61K 8/64* (2013.01); *A61Q 19/08* (2013.01); *C07K 5/1019* (2013.01)

(58) Field of Classification Search
None
See application file for complete search history.

(56) References Cited

U.S. PATENT DOCUMENTS

2018/0303743 A1    10/2018  Meng

FOREIGN PATENT DOCUMENTS

| | | | |
|---|---|---|---|
| EP | 2065029 | A1 | 6/2009 |
| EP | 2382963 | A1 | 11/2011 |
| WO | WO-2007/146269 | A2 | 12/2007 |
| WO | WO-2010/004003 | A2 | 1/2010 |

OTHER PUBLICATIONS

International Application No. PCT/EP2021/025445, International Search Report and Written Opinion, mailed Dec. 22, 2021.

*Primary Examiner* — Kevin S Orwig
(74) *Attorney, Agent, or Firm* — MARSHALL, GERSTEIN & BORUN LLP; Andrew M. Lawrence

(57)        ABSTRACT

A tetrapeptide, capable of inducing dermal extracellular matrix protein upregulation, selected from the group consisting of tetrapeptides having the amino acid sequence U-QTAV-Z wherein Q denotes Glutamine, T denotes Threonine, A denotes Alanine and V denotes Valine, at the N-terminal end, U is independently selected from the group consisting of octanoyl (C8), decanoyl (C10), lauroyl (C12), myristoyl (C14), palmitoyl (C16), stearoyl (C18), biotinoyl, elaidoyl, oleoyl, lipoyle, at the C-terminal end, Z is selected from the group consisting of OH, O R1, NHR1 or NR1R2, R1 and R2 are independently selected from the group consisting of alkyl, aryl, aralkyl, alkylaryl, alkoxy, saccharide and aryloxy group, which may be linear, branched, cyclical, polycyclic, unsaturated, hydroxylates, carbonylated, phosphorylated and/or sulphurous, said groups comprising from 1 to 24 carbon atoms and being capable of including one or more heteroatoms O, S and/or N.

6 Claims, 1 Drawing Sheet

Specification includes a Sequence Listing.

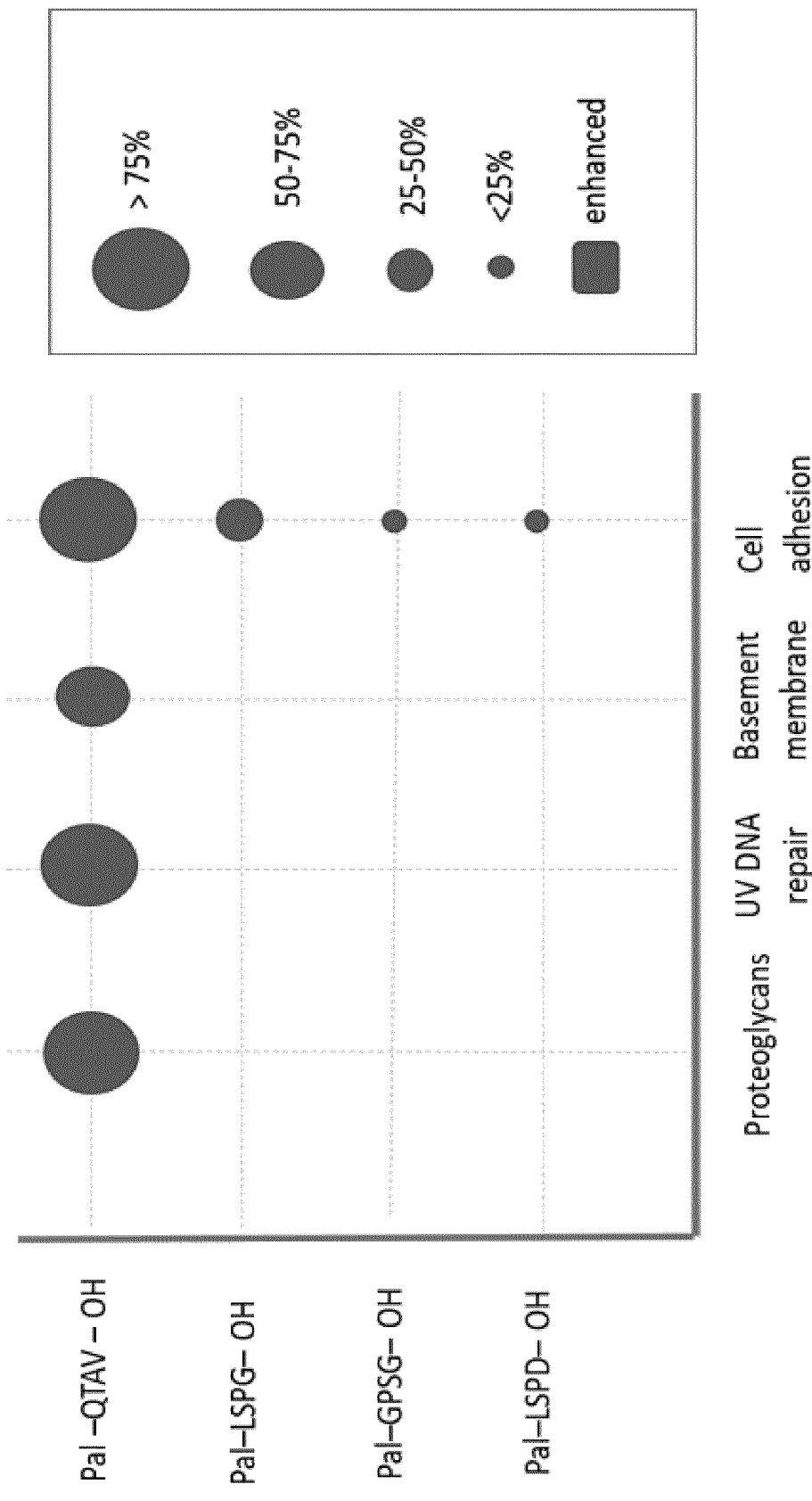

TETRAPEPTIDE AND COMPOSITIONS COMPRISING TETRAPEPTIDES

CROSS REFERENCE TO RELATED APPLICATIONS

This application is the U.S. national phase of PCT Application No. PCT/EP2021/025445, filed on Nov. 16, 2021, which claims priority to European Application No. 20020538.3, filed Nov. 17, 2020, the entire disclosures of which are hereby incorporated by reference in their entirety.

TECHNICAL FIELD

The present invention relates to novel tetrapeptides for use in cosmetic beauty applications and compositions comprising said tetrapeptides.

BACKGROUND TO THE INVENTION

The largest component of normal skin is the dermal extracellular matrix (ECM) which is a gel-like matrix produced by the cells that it surrounds. The ECM comprises two major elements, structural proteins and proteoglycans. Changes to skin come about naturally over time (ageing) as a result of changes in the composition and crosslinked state of the elements of the ECM which cause changes at the structural and behavioural level. Structural changes affect the integrity of the skin. Ageing skin exhibits both an increased degradation of dermal extracellular matrix (ECM) proteins (such as collagen, laminin, elastin, fibronectin) and reduced production of same proteins.

Cellular behavioural changes influence the rate of cell differentiation and proliferation, and therefore the rate of skin repair and renewal. The ECM is also believed to be responsible for producing cell signals which facilitate epithelial cell proliferation and migration, further influencing the skins ability to repair. Changes in the ECM also affect cell-adhesion, signalling, and cell-behaviour mediation.

Particularly important ECM proteins include collagen, fibrillin, fibronectin and decorin. Collagen is responsible for providing elements of the structural integrity of the skin. Collagen in the dermal matrix is composed primarily of type I (80-85%) and type III (8-11%) collagens, both of which are fibrillar, or rod-shaped, collagens. The tensile strength of skin is predominately produced through the fibrillar cross-linked arrangement of the molecules of collagen I. There are also other functionally important although less abundant collagen types in skin, including collagen IV located at the basement membrane of the dermal epidermal junction. This forms sheet-like structures and is more pliable than the fibrillar collagens. Damage to the collagen network of the skin, by for example, free-radical damage, induces the generation of collagen fragments in the ECM, followed by skin regeneration and repair.

Fibrillin is a component of elastic fibres in the ECM and also contributes to the structural integrity of the skin. The most abundant fibrillin in elastic fibres of skin is the FBN1 encoded protein, fibrillin 1.

Fibronectin is glycoprotein of the ECM and is primarily responsible for mediating a wide variety of cellular interactions within the dermal extracellular matrix (ECM), playing an important role in cell adhesion, migration, growth and differentiation.

Decorin (DCN) is a proteoglycan, belonging to the leucine-rich proteoglycan (SLRP) family. The peptide is believed to be important as a component of connective tissue and binds to type I collagen, regulating collagen ECM assembly.

Ageing changes in the skin can occur intrinsically as a consequence of time and extrinsically as a consequence of external mechanisms, including UV-related damage and pollution. Extrinsic mechanisms can result in the increased availability of reactive oxygen species (UV-ROS). These reactive species are known to cause ECM fragmentation and the upregulation of Matrix Metallopeptidases (MMPs) and other ECM proteases. ECM fragmentation may bring about damage to and/or remodelling of the structural ECM proteins and reduce the integrity of the skin.

The fragmentation of ECM proteins can also result in the release of small bioactive peptides or matrikines which act as cell signalling molecules promoting skin repair by upregulating protein production, cell proliferation and differentiation. Both intrinsic and extrinsic ageing can lead to protein fragmentation and the subsequent release of bioactive peptide matrikines.

A number of natural and synthetic peptide matrikines have been used in cosmetic compositions and products for a number of years to stimulate peptide upregulation, skin repair and regeneration. The most commonly used peptide are Pal-KKTKS and the combination of palmitoyl oligopeptide (Pal-GHK), which acts as a messenger peptide for collagen renewal and consists of a sequence derived from collagen I, and palmitoyl tetrapeptide-7 (Pal-GQPR), which reduces the production of interleukin-6 (IL-6), therefore acting as anti-inflammatory and inhibiting ECM degradation, with sequence derived from immunoglobulin G. The said peptide combinations are available from Sederma under the trade names Matrixyl and Matrixyl 3000.

Whilst a number of natural and synthetic peptides have been in use for a number of years there remains a need to identify new and improved biologically active peptides to support the skin's natural behaviours.

SUMMARY OF THE INVENTION

According to the present invention there is provided a tetrapeptide capable of inducing dermal extracellular matrix protein upregulation, selected from the group consisting of tetrapeptides having the amino acid sequence U-QTAV-Z wherein Q is used to denote amino acid Glutamine, T is used to denote amino acid Threonine, A is used to denote amino acid Alanine and V is used to denote amino acid Valine, at the N-terminal end, U is selected from the group consisting of H, —$SO_2$—$R^1$ or a biotinyl group, at the C-terminal end, Z is selected from the group consisting of OH, O $R^1$, NHR$^1$ or NR$^1$R$^2$. $R^1$ and $R^2$ are independently selected from the group consisting of alkyl, aryl, aralkyl, alkylaryl, alkoxy, saccharide and aryloxy group, which may be linear, branched, cyclical, polycyclic, unsaturated, hydroxylates, carbonylated, phosphorylated and/or sulphurous, said groups comprising from 1 to 24 carbon atoms and being capable of including one or more heteroatoms O, S and/or N.

In one aspect, the present invention provides a tetrapeptide, capable of inducing dermal extracellular matrix protein upregulation, selected from the group consisting of tetrapeptides having the amino acid sequence U-QTAV-Z wherein Q is used to denote amino acid Glutamine, T is used to denote amino acid Threonine, A is used to denote amino acid Alanine and V is used to denote amino acid Valine, at the N-terminal end, U is independently selected from the group consisting of octanoyl (C8), decanoyl (C10), lauroyl (C12), myristoyl (C14), palmitoyl (C16), stearoyl (C18), biotinoyl, elaidoyl, oleoyle, lipoyle, at the C-terminal end, Z is selected from the group consisting of OH, O $R^1$, $NHR^1$ or $NR^1R^2$, $R^1$ and $R^2$ are independently selected from the group consisting of alkyl, aryl, aralkyl, alkylaryl, alkoxy, saccharide and aryloxy group, which may be linear, branched, cyclical, polycyclic, unsaturated, hydroxylates, carbonylated, phosphorylated and/or sulphurous, said groups comprising from 1 to 24 carbon atoms and being capable of including one or more heteroatoms O, S and/or N.

BRIEF DESCRIPTION OF THE DRAWINGS

FIG. 1 is a bubble plot showing changes in protein synthesis abundance for four protein families in response to a tetrapeptide of the present invention as well as control tetrapeptides.

DETAILED DESCRIPTION OF THE INVENTION

The present invention is directed toward tetrapeptides that act as signalling matrikines to upregulate the production of proteins of the dermal extracellular matrix (ECM), including at least fibrillin, fibronectin, decorin and collagen I.
Tetrapeptides A tetrapeptide, capable of inducing dermal extracellular matrix protein upregulation, selected from the group consisting of tetrapeptides having the amino acid sequence U-QTAV-Z wherein Q is used to denote amino acid Glutamine, T is used to denote amino acid Threonine, A is used to denote amino acid Alanine and V is used to denote amino acid Valine. At the N-terminal end, U is selected from the group consisting of H, —CO—$R^1$, —$SO_2$—$R^1$ or a biotinyl group. At the C-terminal end, Z is selected from the group consisting of OH, $OR^1$, $NHR^1$ or $NR^1R^2$. $R^1$ and $R^2$ are independently selected from the group consisting of alkyl, aryl, aralkyl, alkylaryl, alkoxy, saccharide and aryloxy group, which may be linear, branched, cyclical, polycyclic, unsaturated, hydroxylates, carbonylated, phosphorylated and/or sulphurous, said groups comprising from 1 to 24 carbon atoms and being capable of including one or more heteroatoms O, S and/or N.

Where, at the N-terminal, U is H then the amino acid is not modified. When, at the C-terminal, Z is OH then the amino acid is not modified. The tetrapeptide is thus not in derivatised form. When other than U is H and Z is OH, then the tetrapeptide is derivatised. Derivation of the tetrapeptide is intended to increase the bioavailability of the peptide by improving the ability of the tetrapeptide to pass through the skin. An increase in bioavailability can also be achieved through vectoring, for example by encapsulation of the peptide.

In a preferred embodiment of the present invention the tetrapeptide is modified at the N-terminal and/or the C-terminal end.

In a preferred embodiment of the present invention, $R^1$ and/or $R^2$ is an alkyl chain of from 1 to 24 carbon atoms, preferably a lipophilic alkyl chain of 3 to 24 carbon atoms.

In a further preferred embodiment of the present invention U is an acyl group —CO—$R^1$ and Z is selected from the group consisting of OH, methoxy, ethoxy and $NH_2$, preferably OH. In a further embodiment, U is preferably independently selected from the group consisting of octanoyl (C8), decanoyl (C10), lauroyl (C12), myristoyl (C14), palmitoyl (C16), stearoyl (C18), biotinoyl, elaidoyl, oleoyle and lipoyle. In a preferred embodiment of the present U is selected from lauroyl (C12), myristoyl (C14) and palmitoyl (C16).

In a further preferred embodiment Z is OH and U is independently selected from the group consisting of palmitoyl (C16), myristoyl (C14) and lauroyl (C12). Most preferably Y is palmitoyl (C16) and Z is OH.

The tetrapeptides may comprise amino acids in the D- or L-configuration. The tetrapeptides may comprise an acid C-terminus such as —CO2H. Alternatively, the tetrapeptide may comprise an amide C-terminus such as —CONH2, —CONHR or CONR2, wherein R is an alkyl chain.

The amino acids making up the tetrapeptides according to the invention may be optically pure, be made up of L or D isomers or a mixture of them. L isomers are those present in the natural state and may be preferred.

The present invention also envisages further derivatives of the tetrapeptide, including for example modification and/or addition of a chemically functional group to one or more of the amino acids but without a change in the carbon skeletal. The present invention also envisages further analogues of the tetrapeptide, including modification and/or addition of a chemically functional group to one or more of the amino acids with a change in the carbon skeletal and complexes of the tetrapeptide with other species such as a metal ion (e.g. copper, zinc, manganese, magnesium, and others).

Tetrapeptides may be found in the form of salts, including hydrochloric salt, or acetate.
Excipient Composition The tetrapeptides of the present invention are provided by the supplier to the cosmetic composition formulator as a concentrated excipient composition. The excipient composition is therefore a cosmetic composition ingredient. The excipient composition comprises tetrapeptides at from 250 to 1650 ppm. In an alternative embodiment, the excipient composition comprises tetrapeptides at a level of from 0.1 to 50,000 ppm. In a further alternative embodiment, the excipient composition comprises from 1 to 5,000 ppm. In a further alternative embodiment, the excipient composition comprises tetrapeptide at a level of from 10 to 500 ppm.

The excipient composition, in addition to tetrapeptides, may optionally comprises ingredients selected from the group consisting of water, surfactants, diols, triols, glycerine, thickener and mixtures thereof. All suitable surfactants, diols (also known as glycols), triols, glycerine and thickener ingredients may be incorporated into the present excipient composition. Preferred surfactants for the excipient composition are selected from the group consisting of alkyl polyglucosides (preferably decyl glucoside, coco glucoside, lauryl glucoside), sodium lauroyl lactylate, polysorbate 20, polysorbate 60, sorbitan laurate, PEG/PPG-18/18 dimethicone, Cetyl PEG/PPG-10/1 dimethicone, Polyglyceryl-4 isostearate, Hexyl laurate, steareth-21, steareth-2 and mixtures thereof.

Preferred diols are selected from the group consisting of pentylene glycol, caprylyl glycol, butylene glycol, di-propylene glycol, of ethylhexylglycerine, propanediol, hexenediol, glycerol, butylene glycol, propylene glycol, isoprene glycol, dipropylene glycol, pentylene glycol, hexylene glycol, polypropylene glycol, butylene glycol, polyethylene glycol, sorbitol, glucitol, mannitol, hydroxypropyl sorbitol, erythritol, threitol, pentaerythritol, xylitol.

Preferred triols are selected from the group consisting hexanetriol, glycerine, ethoxylated glycerin, propoxylated glycerin and mixtures thereof.

The excipient composition may comprise a thickener. Non-limiting examples of various types of thickeners include:

a. Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol. Examples of commercially available carboxylic acid polymers useful herein include the carbomers, which are homopolymers of acrylic acid crosslinked with allyl ethers of sucrose or pentaerythritol. The carbomers are available as the CARBOPOL 900 series from Lubrizol (e.g., Carbopol® 980). In addition, other suitable carboxylic acid polymeric agents include Ultrez® 10 or Ultrez® 30 (Lubrizol) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol.

These copolymers are known as acrylates/C10-C30 alkyl acrylate crosspolymers and are commercially available as Carbopol® 1382, Ultrez® 21, Pemulen TR-1, Pemulen TR-2 and Pemulen EZ-4U from Lubrizol. In other words, examples of carboxylic acid polymer thickeners useful herein are those selected from carbomers, acrylates/C10-C30 alkyl acrylate crosspolymers, and mixtures thereof.

b. Crosslinked Polyacrylate Polymers

The compositions of the present disclosure can optionally contain crosslinked polyacrylate polymers useful as thickeners or gelling agents including both cationic and nonionic polymers. Examples of crosslinked polyacrylate polymers include Polyacrylate crosspolymer-6.

c. Polyacrylamide Polymers

The compositions of the present disclosure can optionally contain polyacrylamide polymers, especially nonionic polyacrylamide polymers including substituted branched or unbranched polymers. Among these polyacrylamide polymers is the nonionic polymer given the CTFA designation polyacrylamide and isoparaflin and laureth-7, availableunder the Tradename Sepigel 305 from Seppic. Other polyacrylamide polymers useful herein include multi-block copolymers of acrylamides and substituted acrylamides with acrylic acids and substituted acrylic acids. Commercially available examples of these multi-block copolymers include Hypan 5R150H, 55500V, SSSOOW, SSSA100H, from Lipo Chemicals, Inc. The compositions may also contain thickening and texturising gels of the type as exemplified by the product range 40 called Lubrajel® from United Guardian. These gels have moisturizing, viscosiFying, stabilizing properties.

d. Polysaccharides

A wide variety of polysaccharides can be useful herein. "Polysaccharides" refer to gelling agents that contain a 45 backbone of repeating sugar (i.e., carbohydrate) units. Non-limiting examples of polysaccharide gelling agents include those selected from the group consisting of cellulose, carboxymethylhydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Also useful herein are the alkyl-substituted celluloses.

e. Gums

Other thickening and gelling agents useful herein include materials which are primarily derived from natural sources. Nonlimiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, scierotiurn gum, sodium carboxymethyl dcxtran,sodium carrageenan, tragacanth gum, xanthan gum, biosacharide gum, and mixtures thereof. Additional examples of water-soluble thickeners include water-soluble natural polymers, water-soluble synthetic polymers, clay minerals and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, farcelluran,agar, high-methoxy pectin, low-methoxy pectin, xanthine,chitosan, starch, fermentation polysaccharide (for example,xanthan gum, pullulan, carciran, dextran), acidic heteropolysaccharidederiv ed form callus of plants belonging to *Polyantes* sp. (for example, tuberous polysaccharide), proteins (for example, sodium casein, gelatin, albumin), chondroitinsulfate, and hyaluronic acid. Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropylcellulose, hydroxyethyl cellulose, hydroxypropyl cellulose, cellulose sulfate sodium salt), Additionally, the one or more thickeners may include polymeric thickeners selected from the group consisting of ammonium polyacryloyldimethyl taurate, ammonium acryloyldimethyltaurate/VP copolymer, sodium polyacrylate, acrylates copolymers.

Preferred thickeners are selected from the group consisting of xanthan gum, ammonium acryloyldimethyltaurate/ vinyl pyrrolidone copolymer, dimethicone crosspolymer, carbomer, hydroxyethyl cellulose, polyacrylamide, polyacrylate crosspolymer-6, and mixtures thereof.

Cosmetic Composition

The present invention also encompasses cosmetic compositions comprising tetrapeptides of the present invention. The tetrapeptides are preferably incorporated into the cosmetic composition in amounts of from to 10,000 ppm, preferably from 0.50 ppm to 5,000 ppm, more preferably from 1 ppm to 1000 ppm, and most preferably from 1 ppm to 500 ppm. These are again based on a % w/w basis. Thus 100,000 ppm is 10% by weight of the emulsion.

A cosmetic composition is a product designed for use by a consumer and is preferably a facial skincare cosmetic composition.

The cosmetic composition of the present invention may be aqueous or non-aqueous and comprise of a single-phase system or multiple phase system. The composition may include but is not limited to liquids, gels, balms, oils or solids. Single or multiple phase compositions are envisaged. Multiple phase systems include but are not limited to microemulsions, emulsions, and products with discrete separate phases. Emulsions include water-in-oil, oil-in-water emulsions and multiple emulsions (water in oil in water or oil in water in oil for example). Products with discrete separate phases include bi or triphasic systems where the individual water or oil phases can be visibly seen.

Where the composition is aqueous, it preferably comprises from 10% to 99.9% by weight water. In a preferred embodiment, aqueous compositions comprise from 20% to 80% by weight water. In a preferred embodiment, aqueous compositions comprise from 40% to 70% by weight water. Where the composition is non-aqueous it preferably comprises 0% to up to 10% water, more particularly from 0.1 to 8%, most preferably from 0.5 to 5% water.

Where the composition is an emulsion it comprises an oil and a water phase. The oil phase of an emulsion can be provided by any suitable oily component. Suitable oils for the oil phase may comprise for example: a) hydrocarbon oils, such as paraffin or mineral oils; b) waxes, such as beeswax or paraffin wax; c) natural oils, such as sunflower oil, apricot kernel oil, shea butter or jojoba oil; d) silicone oils, such as dimethicone, silicone elastomer, cyclomethicone or cetylidimethicone; e) fatty acid esters and ethers, such as isopropyl palmitate or isopropyl myristate and polypropylene glycol-15 stearyl ether; f) fatty alcohols, such as cetyl alcohol or stearyl alcohol; or g) mixtures thereof, for example, the blend of waxes available commercially under the trade name Cutina (BASF).

The emulsion may comprise 0.1% to 55% by weight of the emulsion of oil phase. In one embodiment, the emulsion may comprise 3% to 25% by weight of the emulsion of oil phase, more preferably from 5% to 20% by weight of the emulsion of oil phase. In an alternative embodiment, the emulsion may comprise 10% to 50% by weight of the emulsion of oil phase, more preferably from 25-50% by weight of the emulsion of oil phase.

Preferably the oil phase of the emulsion comprises oil at a level between 50% and 100% by weight of the oil phase. More preferably the oil phase comprises oil at a level of from 60% to 100%, more preferably from 70% to 100%, and even more preferably from 80% to 100% by weight of the oil phase. Alternatively, the oil phase of the emulsion may comprise a combination of oil, wax or butter. Waxes and butters are hydrocarbons that consist of long aliphatic alkyl chains and may include aromatic groups. They are generally lipophilic and typically solid or malleable at room temperature. Melting points vary depending on the alkyl chain, chain length and associations. Silicone waxes are preferred type of suitable wax based on alkylmethylsiloxane. Oils are typically lipophilic and liquid at room temperature with lower molecular weights than waxes. Where present wax or butter may be present at up to 40% of the oil phase of the emulsion. More preferably the oil phase may contain wax or butter at levels of up to 20% of the oil phase of the emulsion. In an alternative embodiment the oil phase may contain wax or butter at levels of up to 10% of the oil phase of the emulsion.

Preferably the oil phase of the water-in-oil emulsion comprises a silicone oil. Where present, the silicone-containing oil phase preferably comprises an organo polysiloxane oil. The organopolysiloxane oil for use in the composition may be volatile, non-volatile, or a mixture of volatile and non-volatile silicones. The term "non-volatile" as used in this context refers to those silicones that are liquid or gel under ambient conditions and have a flash point (under one atmosphere of pressure) of greater than 100° C. The term "volatile" as used in this context refers to all other silicone oils. Suitable organopolysiloxanes can be selected from a wide variety of silicones spanning a broad range of volatilities and viscosities. Examples of suitable organopolysiloxane oils include polyalkylsiloxanes, cyclic polyalkylsiloxanes, and polyalkylarylsiloxanes.

Preferred for use herein are organopolysiloxanes selected from the group consisting of polyalkylsiloxanes which include low, medium and high molecular weight dimethicone and dimethiconols alkyl substituted dimethicones such as cetyl dimethicone and caprylyl methicone, cyclic organopolysiloxanes having from 3 to 6 silicon atoms are included, for example, octamethylcyclotetrasiloxane, decamethylcyclopentasiloxane, dodecamethylcyclohexasiloxane etc, These are termed cyclomethicones. Also included are silicone resins of the type MQ and T-Propyl also know as trimethylsiloxysilicates and polypropylsilsesquioxane, polyalkylaryl siloxanes, and mixtures thereof. More preferred for use herein are polyalkylsiloxanes and cyclomethicones. Preferred among the polyalkylsiloxanes are dimethicones.

Alternatively, the silicone oil may be a silicone elastomer. Suitable for use herein are silicone elastomers which can be emulsifying or non-emulsifying crosslinked siloxane elastomers or mixtures thereof. No specific restriction exists as to the type of curable organopolysiloxane composition that can serve as starting material for the crosslinked organopolysiloxane elastomer. Examples in this respect are addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl-terminated diorganopolysiloxane and SiH-containing diorganopolysiloxane and condensation-curing organopolysiloxane compositions which cure in the presence of an organotin compound or a titanate ester.

Preferably the oil phase comprises silicone, and most preferably, a silicone elastomer. Preferably, the emulsion composition includes from 20% to 35%, by weight of the emulsion composition, of the silicone elastomer raw material.

When the composition is a water-in-oil emulsion it preferably comprises an emulsifier. In a preferred embodiment, the composition comprises from 0.1% to 10% emulsifier, more preferably from 0.25% to 7.5%, still more preferably from 0.5% to 5%, emulsifier by weight of the composition. The emulsifier helps disperse and suspend the aqueous water phase within the oil phase.

Emulsifiers

The composition of the present invention may comprise an emulsifier. Suitable emulsifiers include all those suitable for the purpose and known by those skilled in the art for use in skin care products. Preferably these emulsifiers have an HLB value of or less than 14, more preferably from 2 to 14, and still more preferably from 4 to 14.

Silicone emulsifiers are preferred. A wide variety of silicone emulsifiers are useful herein. These silicone emulsifiers are typically organically modified organopolysiloxanes, also known to those skilled in the art as silicone surfactants. Useful silicone emulsifiers include dimethicone copolyols. These materials are polydimethyl siloxanes which have been modified to include polyether side chains such as polyethylene oxide chains, polypropylene oxide chains, mixtures of these chains, and chains comprising moieties derived from both ethylene oxide and propylene oxide. Other examples include alkyl-modified dimethicone copolyols, i. e., compounds which comprise C2-C30 pendant side chains. Still other useful dimethicone copolyols include materials having various cationic, anionic, amphoteric and zwitterionic pendant moieties.

Nonlimiting examples of dimethicone copolyols and other silicone surfactants useful as emulsifiers herein include polydimethylsiloxane polyether copolymers with pendant polyethylene oxide side chains, polydimethylsiloxane polyether copolymers with pendant polypropylene oxide side chains, polydimethylsiloxane polyether copolymers with pendant mixed polyethylene oxide and polypropylene oxide side chains, polydimethylsiloxane polyether copolymers with pendant mixed poly (ethylene) (propylene) oxide side chains, polydimethylsiloxane polyether copolymers with pendant organobetaine side chains, polydimethylsiloxane polyether copolymers with pendant carboxylate side chains, polydimethylsiloxane polyether copolymers with pendant quaternary ammonium side chains; and also further modifications of the preceding copolymers comprising pendant C2-C30 straight, branched, or cyclic alkyl moieties. A particularly preferred emulsifier is PEG/PPG-18/18 dimethicone.

Suitable, cetyl dimethicone copolyol is commercially available as a mixture with polyglyceryl-4 isostearate (and) hexyl laurate or as a mixture with hexyl laurate and polyglyceryl-3 oleate. Other nonlimiting examples of dimethicone copolyols also include lauryl dimethicone copolyol, dimethicone copolyol acetate, diemethicone copolyol adipate, dimethicone copolyolamine, dimethicone copolyol behenate, dimethicone copolyol butyl ether, dimethicone copolyol hydroxy stearate, dimethicone copolyol isostearate, dimethicone copolyol laurate, dimethicone copolyol methyl ether, dimethicone copolyol phosphate, and dimethicone copolyol stearate.

Among the non-silicone-comprising emulsifiers useful herein are various non-ionic and anionic emulsifying agents such as sugar esters and polyesters, alkoxylated sugar esters and polyesters, C1-C30 fatty acid esters of C1-C30 fatty alcohols, alkoxylated derivatives of C1-C30 fatty acid esters of C1-C30 fatty alcohols, alkoxylated ethers of C1-C30 fatty alcohols, polyglyceryl esters of C1-C30 fatty acids, C1-C30 esters of polyols, C1-C30 ethers of polyols, alkyl phosphates, polyoxyalkylene fatty ether phosphates, fatty acid amides, acyl lactylates, soaps, and mixtures thereof. Nonlimiting preferred examples of these non-silicon-comprising emulsifiers include: polyethylene glycol 20 sorbitan monolaurate (Polysorbate 20), polyethylene glycol 5 soya sterol, Steareth-20, Ceteareth-20, PPG-2 methyl glucose ether distearate, Ceteth-10, Polysorbate 80, cetyl phosphate, potassium cetyl phosphate, diethanolamine cetyl phosphate, Polysorbate 60, glyceryl stearate, PEG-100 stearate, polyoxyethylene 20 sorbitan trioleate (Polysorbate 85), sorbitan monolaurate, polyoxyethylene 4 lauryl ether sodium stearate, polyglyceryl-4 isostearate, hexyl laurate, steareth-20, ceteareth-20, PPG-2 methyl glucose ether distearate, ceteth-10, diethanolamine cetyl phosphate, glyceryl stearate, PEG-100 stearate, and mixtures thereof.

Further Peptides

The compositions of the present invention may comprise further peptides. Preferably said additional peptides are selected from the group consisting of dipeptides, tripeptides, additional tetrapeptides, pentapeptides and mixtures thereof. By tripeptides, it is meant compound comprising an uninterrupted sequence of three amino acids. By tetrapeptides, it is meant a compound comprising an uninterrupted sequence of four amino acids and when using further tetrapeptides, the tetrapeptides are referred to as 'additional tetrapeptides'. By pentapeptide it is meant a compound comprising an uninterrupted sequence of five amino acids.

Dipeptides:

The compositions of the present invention may comprise a dipeptide selected from the group consisting of acetyl dipeptide 1 cetyl ester, acetyl dipeptide 3 aminohexanoate, azelaoyl bisdipeptide 10, coumaroyl dipeptide 3, dicetyl dipeptide 9, dipeptide diamino butyroyl benzylamide diacetate, dipeptide 1, dipeptide dipeptide 11, dipeptide 12, dipeptide 15, dipeptide 16, dipeptide 17, dipeptide 18, dipeptide 19, dipeptide 2, dipeptide 20, dipeptide 3, dipeptide 4, dipeptide 5, dipeptide 6, dipeptide 7, dipeptide 8, dipeptide 8 HCL, dipeptide 9, hexanoyl dipeptide 3 norleucine acetate, methyl undecylenoyl dipeptide 16, nicotinoyl dipeptide 22, nicotinoyl dipeptide 23, nicotinoyl dipeptide 24, nicotinoyl dipeptide 26, oleoyl dipeptide 15, palmitoyl dipeptide 10, palmitoyl dipeptide 13, palmitoyl dipeptide17, palmitoyl dipeptide 5 diaminobutyroyl hydroxythreonine, palmitoyl dipeptide 5 diaminohydroxybutyrate, palmitoyl dipeptide 7 and mixtures thereof.

Dipeptides are preferably incorporated into the cosmetic composition of the present invention at a level of from 0.1 to 50000 ppm, more preferably from 1 to 5000 ppm, most preferably from 10 to 500 ppm.

Tripeptides:

The emulsions of the present invention preferably comprise a tripeptide. Said tripeptide may be naturally occurring or of synthetic origin. Suitable tripeptides include tripeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, derivatives thereof and mixtures thereof.

Particularly preferred tripeptides comprise one or more His-based tripeptides. However, another suitable tripeptide may be Arg-Lys-Arg. Particularly preferred tripeptides are based on the structure GlU-His-Lys and its analogs and derivatives thereof. These are collectively known herein as GHK-tripeptides. Indeed, the preferred tripeptide in accordance with this aspect of the invention has this exact sequence of amino acids. Analogs of the preferred tripeptide useful herein include those in which one or more of the three amino acids are reorganized or rearranged within the sequence (e.g., GlU-Lys-His) and/or where no more than two amino acids are substituted (e.g., His-Ala-Orn). However, most preferably, amino acids substituted for Gly include an aliphatic side chain such as, without limitation, beta-Ala, Ala, Val, Leu, Pro, Sarcosine (Sar) and Ile. Most preferred are Ala, Leu and Ile. The most preferable amino acid substituted for Lys or His include those having a side chain that includes, predominantly, a charged nitrogen at a pH of 6, such as, without limitation, Pro, Lys, Arg, His, Desmosine and Isodesmosine. Most preferably, Lys is replaced with Orn, Arg, or Citrulline.

Derivatives are also considered to be encompassed by the term GHK-tripeptides in accordance with the present invention, (and therefore also the more generic term tripeptides). Derivatives of GHK-tripeptides in accordance with the present invention include derivatives of the substituted and rearranged tripeptides described herein. These derivatives include, inter alia, acyl-derivatives, which are tripeptides substituted with one or more straight-chain or branched-chain, long or short chain, saturated or unsaturated, substituted with a hydroxy, amino, acyl amino, sulfate or sulfide group, or unsubstituted, which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or sulphur comprising groups such as, without limitation $SO_3H$, SH or S—S.

His-based tripeptides include at least one Histidine amino acid. The other two amino acids in the sequence may be the same or different. Thus, contemplated are, without limitation, His-Xaa-Xaa, His-Xaa-Xbb, His-Xbb-Xaa, Xbb-His-Xbb, Xbb-His-Xaa, Xaa-His-Xbb, Xaa-Xaa-His, Xaa-Xbb-His, Xbb-Xaa-His and Xbb-Xbb-His, where Xaa and Xbb are two different amino acids, although either can be His. Preferably, at least one of the other amino acids is Gly, beta-Ala, Ala, Val, Leu, Pro, Sarcosine (Sar) or Ile. Preferably, at least one of the other amino acids is Pro, Lys, Arg, His, Desmosine and Isodesmosine. Most preferably, Lys is replaced with Orn, Arg, or Citrulline.

Derivatives are also considered to be encompassed by the term His-based tripeptides in accordance with the present invention, (and therefore also the more generic term tripeptides). These derivatives include, inter alia, acyl-derivatives, which are tripeptides substituted with one or more straight-chain or branched-chain, long or short chain, saturated or unsaturated substituted or unsubstituted acyl group(s) having from 1 to 29 carbon atoms. The acyl groups which can be used are the same as those described for the GHK-tripeptides.

Particularly preferred embodiments of tripeptides in accordance with the present invention include N-Acyl-GlU-His-Lys and most preferably, N-Palmitoyl-GlU-His-Lys. Preferred commercially available tripeptide and tripeptide derivative comprising compositions include Biopeptide-CL from SEDERMA, Maxilip® from SEDERMA, Biobustyl® from SEDERMA.

The tripeptides where included are preferably incorporated into the cosmetic composition in amounts of from 0.10 ppm to 10,000 ppm, preferably from 0.50 ppm to 5,000 ppm, more preferably from 1 ppm to 1000 ppm, and most preferably from 1 ppm to 500 ppm. These are again based on a % w/w basis. Thus 100,000 ppm is 10% by weight of the emulsion.

Additional Tetrapeptides:

The cosmetic composition may comprise an additional tetrapeptide. These may be one or more rigin-based tetrapeptides, one or more ALAMCAT-tetrapeptides or mixtures thereof. These tetrapeptides may be naturally occurring or of synthetic origin. Suitable tetrapeptides for use in the present composition include those selected from the group consisting of well-known tetrapeptide 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 34, 35, derivatives thereof and mixtures thereof.

Rigin-based tetrapeptides in accordance with the present invention are based on the structure GlU-Gln-Pro-Arg (Rigin) and include its analogs and derivatives thereof. Rigin is an additional tetrapeptide. Analogs of the tetrapeptide rigin useful in accordance with the present invention include those in which one or more of the four amino acids are reorganized or rearranged within the sequence and/or where no more than two of the amino acids are substituted (e.g., Ala-Gln-Thr-Arg. More preferably, at least one of the amino acids within the sequence is Pro or Arg and most preferably the tetrapeptide includes both Pro and Arg although their order and position may vary. The amino acid substitutions can be from amongst any amino acid as defined herein. Particularly preferred rigin-based tetrapeptides include Xaa- Xbb-Arg-Xcc, Xaa-Xbb-Xcc-Pro, Xaa-Xbb-Pro-Arg, wherein Xaa-Xbb-Pro-Xcc, Xaa-Xbb-Xcc-Arg, Xaa, Xbb and Xcc may be the same or different and selected from the following Xaa is Gly or the amino acids that may be substituted therefore, Xbb is Gln or the amino acids that may be substituted therefore and Xcc may be Pro or Arg or the amino acids substituted therefore. The most preferable amino acids substituted for Gly include an aliphatic side chain such as, without limitation, beta-Ala, Ala, Val, Leu, Pro, Sarcosine (Sar) and Ile. The most preferable amino acids substituted for Gln include a side chain that includes an amine group that is predominantly uncharged at neutral pH (pH 6-7) such as, without limitation, Asn, Lys, Orn, 5-hydroxyproline, Citrulline and Canavanine. When Arg is substituted, it is preferably replaced with an amino acid having a side chain that includes, predominantly, a charged nitrogen at a pH of 6, such as, without limitation, Pro, Lys, His, Desmosine and Isodesmosine.

Derivatives are also considered to be encompassed by the term rigin-base tetrapeptides, (and therefore also the more generic term tetrapeptides). Derivatives include derivatives of the substituted and rearranged rigin-based tetrapeptides described herein. These derivatives include, inter alia, acyl-derivatives, which are tetrapeptides substituted with one or more straight-chain or branched-chain, long or short chain, saturated or unsaturated, substituted with a hydroxy, amino, amino acyl, sulfate or sulfide group or unsubstituted having from 1 to 29 carbon atoms. N-acyl-derivatives include those acyl groups which can be derived from acetic acid, capric acid, lauric acid, myristic acid, octanoic acid, palmitic acid, stearic acid, behenic acid, linoleic acid, linolenic acid, lipoic acid, oleic acid, isostearic acid, elaidoic acid, 2-ethylhexaneic acid, coconut oil fatty acid, tallow fatty acid, hardened tallow fatty acid, palm kernel oil fatty acid, lanolin fatty acid and the like. Preferable examples of the acyl group include an acetyl group, a palmitoyl group, an elaidoyl group, a myristyl group, a biotinyl group and an octanoyl group. These may be substituted or unsubstituted. When substituted, they are preferably substituted with hydroxyl or sulphur comprising groups such as, without limitation SO3H, SH or S—S.

Derivatives are also considered to include peptide-divalent ion complexes. $Cu^{2+}$-peptide derivatives are preferred as this may provide increased biological effect compared to the peptide alone.

ALAMCAT tetrapeptides are tetrapeptides which include at least one amino acid including an aliphatic group comprising side chain. These amino acids include, without limitation, Gly, beta-Ala, Ala, Val, Leu, Sarcosine (Sar) and Ile. These tetrapeptides also include at least one amino acid including at least one NH2 comprising side chain. These amino acids include a side chain that has an amine group that is predominantly uncharged at neutral pH (pH 6-7) such as, without limitation, Gln, Asn, Lys, Orn, 5-hydroxyproline, Citrulline and Canavanine. The ALAMCAT-tetrapeptides also include at least one amino acid having at least one side chain including at least one cationic amine (predominant species is charged such as NH3+, NH2+, etc.—basic amino acids which are positively charged at pH 6.0). These amino acids include, without limitation, Pro, Arg, Lys, His, Desmosine and Isodesmosine. The remaining amino acid can be any amino acid, but is preferably one comprising an alphatic group, pendant amino group or pendant cationic group. Derivatives are also considered to be encompassed by the term ALAMCAT-tetrapeptides in accordance with the present invention, (and therefore also the more generic term tetrapeptides). These derivatives include, inter alia, acyl-derivatives, which are tetrapeptides substituted with one or more straight-chain or branched-chain, substituted or unsubstituted long or short chain, saturated or unsaturated acyl group(s) having from 1 to 29 carbon atoms. The acyl groups which can be used are the same as those described for the rigin-based tetrapeptides.

Preferred embodiments include Peptide E, arg-ser-arg-lys, N-acyl-GlU-Gln-Pro-Arg peptides, most preferably N-palmitoyl-GlU-Gln-Pro-Arg.

Preferred commercially available sources of tetrapeptides include RIGIN, EYELISS, Haloxyl, and MATRIXYL 3000, which comprise between 50 to 500 ppm of palmitoyl-GlU-Gln-Pro-Arg, and other ingredients, such as peptides, chalcones and an excipient, commercially available from SEDERMA, France. Tego Pep 417 available from Evonik. These may be used to produce compositions of the present invention by adding thereto at least one tripeptide as described herein.

The additional tetrapeptides when used are preferably incorporated in to the cosmetic composition in amounts from 0.1 ppm (0.00001% w/w also referred to herein as "weight percent", "weight %" or simply by weight) to 10,000 ppm (1.0% w/w), preferably from 0.5 ppm to 1000 ppm (0.1% w/w), and most preferably from 1 ppm to 500 ppm (0.05% w/w) by weight of the composition.

The combination of tripeptides and additional tetrapeptides, can be particularly preferred. When present, the preferred ratio of additional tetrapeptide to tripeptide, or indeed the ratio of molecules having four amino acids to those having three amino acids can range from 100:1 to 1:100; more preferably from 50:1 to 1:50, even more preferably from 30:1 to 1:30 and even more preferably between 10:1 to 1:10. Most preferably, the ratio of additional tetrapeptide to tripeptide ranges from between 3:1 to 1:3. These ratios are on a weight basis (% w/w—e.g. mg of pure peptide per Kilogram in the final formulation). In a particularly preferred embodiment, the amount of tripeptide used is greater than the amount of additional tetrapeptide used when considered in terms of their amounts in parts per million, again based on overall weight of the composition. In a particularly preferred embodiment, the cosmetic composition of the present invention comprise an additional tetrapeptide of the sequence GlU-Gln-Pro-Arg, its analogs and derivatives in combination with one or more tripeptide of the sequences GlU-His-Lys, its analogs and derivatives.

Pentapeptides

The compositions of the present invention may optionally comprise a pentapeptide, derivatives of pentapeptides, and mixtures thereof. As used herein, "pentapeptides" refers to both the naturally occurring pentapeptides and synthesized pentapeptides. Also useful herein are naturally occurring and commercially available compositions that comprise pentapeptides. Suitable pentapeptides are those selected from the group consisting of pentapeptidel, 4, 5, 6, 7, 8, 9, 10, 11, 12, 13, 14, 15, 16, 17, 18, 19, 21, 22, 23, 24, 25, 26, 28, 29, 30, 31, 33, 34, 35, 36, 38, 39, derivatives thereof and mixtures thereof.

Suitable pentapeptides for use herein are the pentapeptide, lys-thr-thr-lys-ser, Arg-asp-lys-tyr-val (pentapeptide-1) and derivatives thereof. A preferred commercially available pentapeptide derivative-comprising composition is Matrixyl which comprises 100 ppm of palmitoyl-lys-thr-thr-lys-ser and is commercially available from Sederma, France.

The pentapeptides when used are preferably incorporated in to the cosmetic composition in amounts from 0.1 ppm (0.00001% w/w also referred to herein as "weight percent", "weight %" or simply by weight) to 10,000 ppm (1.0% w/w), preferably from 0.5 ppm to 1000 ppm (0.1% w/w), and most preferably from 1 ppm to 500 ppm (0.05% w/w) by weight of the composition.

Matrix Metalloproteinase Inhibitors (MMPi)

The term "matrix metalloproteinase inhibitor" relates to all molecule and/or plant or bacterial extracts having an inhibitory activity on at least one of the matrix metalloproteinases expressed or synthetized by or in the skin. The family of the matrix metalloproteinases is formed of several well-defined groups on the basis of their resemblance regarding structure and substrate specificity (Woessner J. F. 1991, Faseb Journal, vol. 5,-, 2145). Among these groups, there are collagenases able to degrade fibrillar collagens (MMP-1 or interstitial collagenase, MMP-8 or neutrophil collagenase, MMP-13 or collagenase 3, MMP-18 or collagenase 4), gelatinases degrading type IV collagen or other denatured collagen form (MMP-2 or A gelatinase (72 kDa), MMP-9 or B gelatinase (92 kDa)), stromelysins (MMP-3 or stromelysin 1, MMP-10 or stromelysin 2, MMP-11 or stromelysin 3) whose broad spectrum of activity targets proteins of the dermal extracellular matrix such as glycoproteins (fibronectin, laminin), proteoglycanes etc., matrilysin (MMP-7), metalloelastase (MMP-12) or metalloproteinases (MMP-14, MMP-15, MMP-16 and MMP-17). Metalloproteinases (MMPs) are proteases that use a metal, (mostly zinc) coordinated to 3 cysteine residues and to a methionine in their active site, that degrade macromolecular components of the dermal extracellular matrix and of basal layers at neutral pH (collagen, elastin, etc. . . . ). This group of enzymes is inactivated by metal chelators. The principal activity regulators of MMPs are the tissue inhibitors of metalloproteinases or TIMPs such TIMP-I, TIMP-2, TIMP-3 and TIMP-4 (Woessner J. F., Faseb Journal, 1991). Furthermore, MMP expression is also regulated by growth factors, cytokines, oncogene products (ras, jun), or also matrix constituents.

The term "matrix metalloproteinase inhibitors" according to the present invention means all molecules able to reduce the MMP's activity regarding the gene expression (transcription and translation) or regarding the activation of the zymogen form of the MMP, or else regarding the local control of active forms. Furthermore, the metalloproteinase inhibitors according to the present invention can also be MMP-1 inhibitors of natural or synthetic origin. The terms "natural origin" or "synthetic origin" mean both a metalloproteinase inhibitor at a pure state or in solution at different concentrations, but natural origin termed inhibitors are obtained by different extraction methods from a natural element (for example lycopene from a tomato) whereas the inhibitors of synthetic origin are all obtained via chemical synthesis Preferred MMPi are selected from the group consisting of retinoid, N-acetyl cysteine, glutathione, 2-furildioxime, vitamin C, flavones, isoflavones, hydrolysed rice protein, alfalfa extract, white lupin, zizyphus jujube extract, dihydroxy methyl chromone, kudzu extract, *Vitis vinifera* extract, *Oenothera biennis* extract *Anogeissus leiocarpus* extract and mixtures thereof.

Where present, MMPi are present at a level of from 0.01% to 10%, more preferably 0.1% to 5% and most preferably from 0.5% to 2.5% by weight of the cosmetic composition.

Skin Conditioning Agent

The compositions of the present invention may optionally comprise a skin conditioning agent. Said skin conditioning agents may preferably be selected from the group consisting of humectants, emollients, moisturisers, or mixtures thereof. Where present, they are preferably present at a level of from 0.01% to 20%, more preferably from 0.1% to 10%, most preferably from 0.5% to 7% by weight of the cosmetic composition.

Preferred skin conditioning agents are selected from the group consisting of guanidine, urea, glycolic acid and glycolate salts, salicylic acid, lactic acid and lactate salts, aloe vera, shea butter, polyhydroxy alcohols, such as sorbitol, mannitol, xylitol, erythritol, glycerol, hexanetriol, butanitriol, (di) propylene glycol, butylene glycol, hexylene glycol, polyethylene glycol, sugars (e.g. fructose, glucose, xylose, honey, mannose, xylose), gluconodeltalactone, and starches and their derivatives, pyrrolidone, carboxylic acid, hyaluronic acid and salts thereof, lactamide monoethanolamine, acetamide monoethanolamine, panthenol, allantoin and mixtures thereof.

More preferably said skin conditioning agent is selected from the group consisting of glycerine, arabinogalactan, butylene glycol, hyaluronic acid, shea butter, propylene glycol, ethylhexyl glycerine, hyaluronate and mixtures thereof.

Antioxidant Agent

The compositions of the present invention may optionally comprise an antioxidant agent. Suitable antioxidant agents may include: a) ascorbic acid its salts, esters, glucosides and glucosamines, particularly sodium ascorbyl phosphate, magnesium ascorbyl phosphate and ascorbyl palmitate b) vitamin E (tocopherol) and its esters, particularly tocopheryl acetate, as well as Dimethyl methoxy chromanol which is a synthetic analogue of gamma tocopherol, available from Lipotec S.A. polygon Industrial Camri Ral, under the tradename Lipochroman-6 c) herbal extracts, particularly gingko *biloba*, such as that available under the trade name "Gingko *Biloba* Leaf Powder" from Univar PLC, *morus alba*, such as that available under the trade name "Mulberry Concentrate" from Solabia, *Origanum vulgare*, such as that available under the trade name "Pronalen *Origanum* HSC" from S Black Ltd, *panax ginseng*, such as that available under the trade name "*Panax ginseng* 1.1 extract 4294" from S Black Ltd or "Phytexcell *Panax ginseng*" available from Croda Chemicals Ltd, birch extract such as those available from Cosmetochem (U. K.) Ltd under the trade names "Super Herbasol Extract Birch" and "HP Herbasol *Betula*" and those available from Blagden Chemicals under the tradenames "Phytelene of Birch" and "Aqueous Spray Dried Birch", *Camellia sinensis*, such as that available under the trade name "Herbal Extract Green Tea 75% Solids" from Nichimen Europe, *Rosmarinus officinalis*, such as that available under the trade name "Pronalen Rosemary" from S. Black, Acerola cherry powder, such as that available as Acerola PE from Gee Lawson, Emblica extract sold under the tradename Emblica™ by Merck Speciality chemicals, and Grape Seed oil, such as that available from Chesham Chemicals Limited.

The amounts of antioxidant agents used in the cosmetic composition are expressed as dry weights, as understood by a man skilled in the art. The total amount of antioxidant agents optionally present in the composition may range from 0.005% to 10% by weight, preferably 0.5% to 5%, most preferably 0.2% to 1.5% by weight of the composition.

Particularly preferred synergistic combinations of antioxidant agents suitable for inclusion in the cosmetic composition of the present invention are selected from the group consisting of: i) *panax ginseng, morus alba* and magnesium ascorbyl phosphate; ii) *panax ginseng, morus alba* and sodium ascorbyl phosphate; iii) *panax ginseng, morus alba* and *Rosmarinus officinalis*; iv) *Ginkgo biloba, phyllanthus emblica* and Dimethylmethoxy chromanol; v) *morus alba*,

*Camellia sinensis* and dimethylmethoxy chromanol; vi) moms alba, *Camellia sinensis* and tocopheryl acetate; vii) *panax ginseng, morus alba* and *Origanum vulgare*, viii) *Camellia sinensis*, tocopheryl acetate and dimethylmethoxy-chromanol, iv) *morus alba*, tocopheryl acatete and dimethylmethoxychromanol.

In these preferred combinations (a) the *panax ginseng* is preferably present in an amount of 0.005% to more preferably 0.01% to 0.05% by weight of the composition; (b) the *morus alba* is preferably present in an amount of 0.0005% to 0.01%, more preferably 0.001% to 0.005% by weight of the composition; (c) the sodium, magnesium ascorbyl phosphate or ethyl ascorbic acid is preferably present in an amount of 0.05% to 2.5%, preferably 0.1% to 2%, most preferably 0.15% to 1.5% by weight of the composition; (d) the *Rosmarinus officinalis* or *Origanum vulgare* or *phyllanthus* emblicais preferably present in an amount of 0.01% to 0.5%, more preferably 0.05% to 0.2% by weight of the composition e) the dimethylmethoxy chromanol is preferably present in an amount of 0.0005% to 0.1%, more preferably from 0.005% to 0.05% by weight of the composition; f) the *Camellia sinensis* is preferably present in an amount of 0.005% to 0.2%, more preferably from 0.01% to 0.1% and the g) Tocoperol acetate is preferably present in an amount of 0.01 to 0.5%, more preferably from 0.05% to 0.25%

Vitamins

The compositions of the present invention may comprise one or more vitamins. The compositions may comprise ascorbates, for example vitamin C, vitamin C derivatives, ascorbic acid, ascorbyl glucoside, ascorbyl palmitate, magnesium ascorbyl phosphate, sodium ascorbyl phosphate and ethyl ascorbic acid. The composition may comprise vitamin B, vitamin B derivatives, vitamin B1 to vitamin B12 and their derivatives. In a further embodiment the composition comprising the Vitamin B3 derivative niacinamide.

In an alternative embodiment of the present the cosmetic composition comprises vitamin K, vitamin K derivatives, vitamin H, vitamin D, vitamin D derivatives and mixtures thereof. In an alternative embodiment of the present the cosmetic composition comprises vitamin E, vitamin E derivatives such as tocopherol and tocopheryl acetate, and provitamins thereof, such as panthenol and mixtures thereof. In a further embodiment the present cosmetic composition comprises retinoid compounds, including retinoic acid, retinaldehyde, retinol and derivatives thereof. In one embodiment the cosmetic composition comprises retinyl palmitate, retinyl acetate, retinyl retinoate, retinyl proprionate, retinyl ascorbate, retinyl linoleate, retinyl retinoate, retinyl sunflowerseedate and mixtures thereof.

The vitamin compounds may be included as the substantially pure material, or as an extract obtained by suitable physical and/or chemical isolation from natural (e. g. plant) sources. In one embodiment, when vitamin compounds are present in the compositions of the instant invention, the emulsion compositions comprise from about 0.0001% to 50%, more preferably from 0.001% to 10%, still more preferably from 0.01% to 8%, and still more preferably from 0.1% to 5%, by weight of the composition, of the vitamin compound.

Salicylic Acid Compound

The compositions of the present invention may comprise a salicylic acid compound, its esters, its salts, or combinations thereof. In one embodiment of the compositions of the present invention, the salicylic acid compound preferably comprises from 0.0001% to 25%, more preferably from 0.001% to 15%, even more preferably from 0.01% to 10%, still more preferably from 0.1% to 5%, and even more preferably from 0.01% to 2%, more preferably 0.1% to 2% by weight of the composition, of salicylic acid.

Sunscreen

The compositions of the present invention may optionally comprise a sunscreen component. The sunscreen may comprise organic or inorganic sun filters or a combination of the two. Suitable inorganic sun filters include those selected from the group consisting of microfine titanium dioxide, microfine zinc oxide, boron nitride and mixtures thereof.

Suitable organic sunscreens include those selected from the group consisting of: a) p-aminobenzoic acids, their esters and derivatives (for example, 2ethylhexyl p-dimethylaminobenzoate), b) methoxycinnamate esters (for example, 2-ethylhexyl p-methoxycinnamate, 2-ethoxyethyl p-methoxycinnamate or a, p-di-(p-methoxycinnamoye-a'-(2ethylhexanoye-glycerin, c) benzophenones (for example oxybenzone), d) dibenzoylmethanes such as 4-(tert-butyl)-4'-methoxydibenzoylmethane, e) 2-phenylbenzimidazole-5 sulfonic acid and its salts, f) alkyl-ss, ss-diphenylacrylates for example alkyl a-cyano-ss, ss-diphenylacrylates such as octocrylene, g) triazines such as 2,4,6-trianilino-(p-carbo-2-ethyl-hexyl-1-oxi)-1,3,5 triazine, h) camphor derivatives such as methylbenzylidene camphor and i) mixtures thereof. Other preferred sunscreen ingredients include those selected from the group consisting of homosalate, Ethylhexyl salicylate, Diethylhexylbutamido triazone, Bis-ethylhexyloxyphenol methoxyphenyl triazine, Diethylamino hydroxybenzoyl hexyl benzoate, Butyl methoxydibenzoylmethane, Methylene bis-benzotriazoyl tetramethylbutylphenol, Polysilicone-15 and mixtures thereof. A sunscreen agent is optionally present in an amount from 0.1 to 10% by weight of the composition.

Other Optional Ingredients

The compositions of the present invention may also optionally comprise one or more of the following optional ingredients. Preservatives may be added to the emulsion such as 2-bromo2-nitropropane-1,3-diol (bronopol, which is available commercially under the trade name Myacide®), benzyl alcohol, diazolidinyl urea, imidazolidinyl urea, methyl paraben, phenoxy ethanol, ethyl paraben, propyl paraben, sodium methyl paraben, sodium dehydroacetate, polyhexamethylenebiguanide hydrochloride, isothiazolone and sodium propyl paraben, suitably in an amount of from 0.01% to 10% by weight of the emulsion.

Thickeners, viscosity modifying agents and/or gelling agents may be added to the emulsion composition, such as acrylic acid polymers e. g. available commercially under the trade name Carbopol or Ultrez (Lubrizol) or modified celluloses e. g. hydroxyethylcellulose available commercially under the trade name Natrosol (Hercules) or hydroxypropylmethyl cellulose, amine oxides, block polymers of ethylene oxide and propylene oxide (for example, those available from BASF Wyandotte under the trade name"Pluronic"®), PVM, MA, or a decadiene crosspolymer (available under the trade name Stabilez 60), ethoxylated fatty alcohols, salt (magnesium chloride, sodium chloride), Aristoflex AVC (Clariant), phthalic acid amide, xanthan gum, sodium polyacrylate, polyvinyl alcohols, fatty alcohols and alkyl galactomannans available under the trade name N-Hance from Hercules, suitably in an amount of from 0.5% to 10% by weight of the composition.

Sequestering agents may be added to the emulsion composition, such as ethylenediamine tetraacetic acid and salts thereof, suitably in an amount of from 0.005% to 0.5% by weight of the composition.

The composition may also include waxes such as cocoa butter suitably in an amount of from 1% to 99% by weight of the composition.

The composition may also comprise suitable, cosmetically acceptable diluents, carriers and/or propellants such as dimethyl ether.

The composition may also include pearlising agents such as stearic monoethanolamide and/or mica, suitably in an amount of from 0.01% to 10% by weight of the composition.

Perfumes may be added suitably in an amount of from 0.01% to 2% by weight of the composition, as may water soluble dyes such as tartrazine, suitably in an amount of from a trace amount (such as 1×10-5%) to 0.1% by weight of the composition.

The composition may also include pH adjusting agents such as sodium hydroxide, aminomethyl propanol, triethanolamine, suitably in an amount of from 0.01% to 10% by weight of the composition. The composition may be buffered by means well known in the art, for example by use of buffer systems comprising succinic acid, citric acid, lactic acid, and acceptable salts thereof, phosphoric acid, mono- or disodium phosphate and sodium carbonate. Suitably, the composition may have a pH between 3 and 10, preferably between 4 and 8.

Methods of Use

The present invention also relates to a method for stimulating the production of dermal extracellular proteins including collagen, fibrillin, fibronectin and decorin in humans with the synergistic tetrapeptide combination of the present invention. The method comprises administering to said human the tetrapeptide composition (e.g. in a cosmetically or therapeutically effective amount) according to the present invention and cosmetic compositions comprising same.

In one embodiment, the invention provides the use of a tetrapeptide or a composition as described herein as a non-therapeutic cosmetic treatment to improve the condition of the skin and/or lines and/or wrinkles and/or imperfections.

In one embodiment, the invention relates to a cosmetic method for improving the condition and/or appearance of the skin and/or lines and/or wrinkles, comprising topically administering a peptide combination or a cosmetic composition of the invention.

EXAMPLES

The present invention is further described by the following examples.

Examples of Tetrapeptide Synthesis

The tetrapeptides of the present invention with generic formulation pal-$X^1X^2X^3X^4$—OH are prepared by peptidic synthesis. In a first step the N-terminal of $X^4$ is coupled with a resin via the terminal acid functionality in the presence of a coupling agent. The N terminal amine is then reacted with the next amino acid in the sequence $X^3$ in the presence of a coupling agent. The same process is repeated until the required sequence is obtained and a suitable C terminal functionality added. Suitable coupling agents include DCC (dicyclohexylcarbodimide)/NHS (N-hydroxysuccinimide) or HBTU (2-(1H-benzotriazole-1-yl)-1,1,3,3-tetramethyl-uronium hexafluorophosphate)/HOBT (1-hydroxy-benzotriazole)). The resulting peptide is then cleaved from the resin in an acidic medium and after precipitation, washing and drying, the peptide is obtained in solid form.

Example of Efficacy

The activities of the tetrapeptides of the present invention were assessed using two different methods A) ELISA assay, B) Immunofluorescence and C) Liquid chromatography tandem mass spectrometry (LC-MS/MS) analysis An ELISA is an immunological assay commonly used to measure presence and abundance of a specific proteins (antibodies, antigens, proteins and glycoproteins) in biological samples. In this case ELISAs are being used to quantify the expression of dermal extracellular proteins collagen-1, decorin, and fibronectin. The quantity of collagen I is evaluated via the quantity of PIP ("carboxU-terminal propeptide of procollagen type I") which is a peptide fragment resulting from the enzymatic degradation of procollagen present outside the fibroblast in the culture supernatant medium.

Immunofluorescence relies on the use of antibodies to label a specific protein with a fluorescent dye such as fluorescein isothiocyanate (FITC). In the following experiments, indirect immunofluorescence is used where a primary antibody first recognises and attaches to the specific protein, in this case fibrillin-1, and then a secondary antibody conjugated with FITC directed against the primary antibody is used for detection.

For all experiments, the control liquid stock was prepared by dissolving the powdered peptides in DMSO (Dimethyl Sulfoxide solvent). Peptide powders were dissolved in DMSO at recommended part per million concentrations and then further diluted in the cell culture medium and combined to obtain the desired peptide ratio.

The tetrapeptides of the present invention were demonstrated to have a surprisingly high impact on the up-regulation of ECM protein production. The test methods and data are presented below.

A) ELISA Assay

Normal human dermal fibroblasts cells (HDFs) were cultured in contact with the tetrapeptides of the present invention, or composition without the peptide (negative control), for 72 hours. Thereafter the cultured supernatants were removed, and the quantity of dermal extracellular proteins determined using an ELISA assay for the protein of interest. For the ELISA quantification, cell viability was calculated using Hoechst staining allowing the quantity of dermal proteins to be weighted to the number of viable cells.

The quantity of collagen I is evaluated using the quantity of PIP ("carboxU-terminal pro-peptide of procollagen type I") which is a peptide fragment resulting from the enzymatic degradation of procollagen present outside the fibroblast in the culture supernatant medium.

Results

The effect of the QTAV tetrapeptide on ECM protein expression by fibroblasts as measured by ELISA (column 1) versus tetrapeptide not conforming to the QTAV structure (column 2) are presented in the table below (table 1). The concentration of peptide in each experiment is listed in the table below. Results are expressed as % increase versus the negative control.

TABLE 1

| | 1 Pal-QTAV-OH (5 ppm) | Sig. | 2 Pal-GYIL-OH (5 ppm) | Sig. |
|---|---|---|---|---|
| Collagen 1 (PIP) | +59% | P < 0.01 | −4% | ns |
| Fibronectin | +87% | p < 0.01 | −23% | P < 0.05 |
| Decorin | +33% | P < 0.01 | +2% | ns |

B) Immunofluorescence

Fibrillin-1 expression was determined using immunofluorescence. Primary human dermal fibroblast (I-IDF) cells were purchased from Promo Cell and came from a 29-year-old female donor. Cells were grown in wells of 96 well black walled clear bottomed plates (Peirce, Thermo Fisher). Cells were cultured in in I-IDF media (PromoCell) supplemented with Basic Fibroblast Growth Factor (recombinant human), 1 ng/ml and Insulin 5 µg/ml. Cells were cultured for 5 days in the presence of the tetrapeptides, changing media and peptides every 48 hours, followed by immunofluorescence assessment. At the time of treatment cells were at passage 3-4. After 5 days the media was discarded, and cells fixed with methanol. The Fibrillin-1 fibre formation was probed using primary Fibrillin-1 monoclonal antibody (11C1.3; mouse monoclonal antibody (Thermo Fisher) 1 in 100 dilution overnight) designed to detect Fibrillin-1 protein. The Fibrillin-1 fibre formation was then probed with a secondary Goat anti-mouse IgG Thermo Fisher (1part antibody in 1000 buffer solution for 1 hour) which includes a fluorescent tag designed to reveal the primary antibody binding pattern.

The antibody binding to Fibrillin-1 fibres was visualised using a Nikon Eclipse 100 microscope fluorescence setting using an excitation lens for fluorescein isothiocyanate (FITC). Images were taken using 6 second UV exposure. ImageJ software was used to quantify the Fibrillin-1 fibre abundance and coverage in each image using a threshold of 235 measuring the fibre density.

Results are expressed as a percentage increase in fibrillin abundance compared to untreated control.

Results

Fibrillin-1 expression by HDF cells treated with tetrapeptides conforming to the QTAV structure (Pal-QTAV-OH) and a tetrapeptide not confirming to the QTAV structure (Pal-GYIL-OH) are presented in table 2. The peptide concentration used offered the highest yield of Fibrillin-1 production.

TABLE 2

| | Pal-QTAV-OH 12.5 ppm | Sig. | Pal-GYIL-OH 10 ppm | Sig. |
|---|---|---|---|---|
| Fibrillin-1 | +84% | P < 0.05 | +3% | ns |

The above results show the marked effect the tetrapeptides of the present invention have on the enhanced production of ECM proteins.

C) Liquid Chromatography Tandem Mass Spectrometry (LC-MS/MS) Analysis

Following incubation with the peptides, liquid chromatography tandem mass spectrometry (LC-MS/MS) was used to quantify the relative abundance differences between proteins identified in the secretome/matrisome, versus an untreated control. HDFs from a 25-year-old donor, plated at 50,000 cells per well, were cultured with either peptide dissolved in cell culture media to achieve a final concentration of 8 ppm or with media without any peptide as a negative control. Treated and control cells were tested in triplicate. The cells were cultured as normal for five days in serum-supplemented media and then for a further two days in serum-free media (seven-day culture in total). The cell media containing the secretome (the proteins secreted by the cell) and the ECM, decellularized by incubation with EDTA (ethylenediaminetetraacetic acid), containing the matrisome (the collection of ECM associated proteins) were collected.

The combined secretome and the matrisome compartments were subsequently analysed by LC-MS/MS using the following protocol.

Proteins were denatured (in urea), reduced (in dithiothreitol) and mechanically disassociated (using ultrasonication) prior to overnight digestion with trypsin (SMART Digest™ trypsin kit; Thermo Fisher). After digestion, samples were a response in the expression of dermal extracellular proteins are provided in table 3 below. The protein family which the protein belongs to is also shown. Mass spectrometry results using peptide sequences, according to the invention (column 1) and not according to the present invention (columns 2, 3 and 4), are also presented within the table for comparison.

TABLE 3

| Protein enhanced | Protein family | 1 Pal-QTAV-OH | Sig | 2 Pal-LSPG-OH | Sig | 3 Pal-GPSG-OH | Sig | 4 Pal-LSPD-OH | sig |
|---|---|---|---|---|---|---|---|---|---|
| CSPG2 | Proteoglycans | 31% | $p < 0.05$ | <1% | ns | 20% | ns | 5% | ns |
| RAD23A | UV DNA repair | 230% | $p < 0.05$ | 94% | ns | 51% | ns | 5% | ns |
| LAMB2 | Basement membrane | 27% | $p < 0.05$ | 22% | ns | 25% | ns | 40% | ns |
| NID1 | Basement membrane | 32% | $P < 0.1$ | 6.60% | ns | 28% | ns | 27% | ns |
| CDH2 | Cell adhesion | 69% | $P < 0.1$ | 10% | ns | 85% | ns | 39% | ns |
| LGALS3 | Cell adhesion | 32% | $P < 0.05$ | 24% | ns | 2% | ns | 5% | ns | cleaned of contaminants up by removal of organic molecules and surfactants using biphasic extraction and desalted using OLIGO™ R3 Reversed Phase Resin (Thermo Fisher).

Samples (200 ng) were ran on an UltiMate® 3000 Rapid Separation Liquid Chromatographer coupled to a Q Exactive™ Hybrid Quadrupole-Orbitrap™ Mass Spectrometer for 90-minutes per sample run. Spectral data was searched again the Uniprot Human proteome database using Mascot v2.5.1. Subsequent protein identification and data-dependent quantification was performed using Progenesis QI. Normalised protein abundances were compared between each peptide treatment and control. Statistical analysis was performed within Progenesis QI using a between sample ANOVA.

The mass spectrometry data for each peptide is shown below in table 3 and FIG. 1. Changes in protein synthesis abundance due to each peptide are described below, including changes to specific proteins and the protein families they belong to (table 3) Proteins (with p<0.01) identified through mass spectrometry were grouped into functional protein families (proteins with similar functions) to give an overview of the impact of each peptide sequence on wider protein expression and hence metabolism within the cell culture system. These protein families were as follows: proteoglycans, UV DNA repair proteins, basement membrane protein and cell-adhesion proteins; functional protein families with a potentially important role in dermal repair and remodelling.

The bubble plot (FIG. 1) shows the global effect on these four protein families in response to each peptide tested. Bubble sizes were calculated by summing the percentage change of all the key proteins within that family that were at least trending towards significantly enhanced (p<0.1 or p<0.05), then allocating a bubble size based on the centile it falls within when taking in to account the enhancement observed across all four protein families and all four peptide sequences tested. In the bubble plot, the larger the bubble size, the stronger the enhancement of proteins within that protein family.

Results

The results of the above mass spectrometry experiments wherein a range of tetrapeptides are applied to HDFs to elicit Treatment of HDFs with peptide pal-QTAV-OH led to an overall enhancement of protein synthesis in comparison to the control. Proteins which were either significantly enhanced or trending towards enhancement in comparison to the untreated control are shown in table 3. Proteins significantly enhanced (p<0.05) include the proteoglycan CSPG2, the UV DNA repair protein RAD23A, the basement membrane protein LAMB2 and the cell adhesion protein LGALS3. Proteins trending towards enhancement (0.05<P<0.1) include the basement membrane protein NID1 and the cell adhesion protein CDH2.

A bubble plot showing proteins families enhanced by peptides of various sequences when HGF cells were treated with various peptide sequences is provided as FIG. 1. The larger the bubble size the stronger the enhancement. The peptide with sequence pal-QTAV-OH was the only sequence to significantly enhance proteoglycans, UV DNA repair proteins, basement membrane proteins and cell adhesion proteins. This same significant enhancement was not seen across these groups with peptides of adifferent sequence.

Excipient Composition

The present include examples of the manufacture of an excipient composition of the present invention.

To form a tetrapeptide excipient composition, the tetrapeptide, as manufactured according to the description, is combined with an oil-based matrix comprising a fatty acid ester, stirred and heated until the tetrapeptide is completely solubilised, and the excipient composition is clear. In a preferred example, 1200 ppm of tetrapeptide is used in the excipient composition.

Excipient Composition

The present include examples of the manufacture of an excipient composition of the present invention.

To form a tetrapeptide excipient composition, the tetrapeptide, as manufactured according to the description, is combined with an oil-based matrix comprising a fatty acid ester, stirred and heated until the tetrapeptide is completely solubilised, and the excipient composition is clear. In a preferred example, 1200 ppm of tetrapeptide is used in the excipient composition.

Examples of Cosmetic Compositions

The tetrapeptides of the present invention may be incorporated into cosmetic compositions, representative examples of which are described below.

Cosmetic Composition 1—Representative Water-In-Oil Emulsion Cosmetic Composition

| Material | % w/w |
| --- | --- |
| Dimethicone | 13.83 |
| Water | 37.11 |
| Glycerin | 5.00 |
| Dimethicone crosspolymer & Dimethcone | 32.31 |
| Butylene glycol | 2.60 |
| PEG/PPG-18/18 dimethicone & Polyglyceryl-4 isostearate & Hexyl laurate | 3.00 |
| Cetyl PEG/PPG-10/1 dimethicone | 2.00 |
| Magnesium sulphate | 0.60 |
| Phenoxyethanol & Methylparaben & Ethylparaben | 0.55 |
| Peptide excipient composition comprising propanediol & Pentylene glycol & Decyl glucoside & Water excipient composition | 3.00 |

Method of Manufacture

1. In the main vessel add Dimethicone, Dimethicone crosspolymer, PEG/PPG-18/18 dimethicone & polyglyceryl-4 isostearate & hexyl laurate and Cetyl PEG/PPG-10/1 dimethicone to make the oil phase.
2. Separately weigh out water, magnesium sulphate, glycerine, phenoxyethanol & methylparaben & ethylparaben and peptide & propanediol & pentylene glycol & decyl glucoside & water stir until solids are dissolved to make the water phase.
3. Add the water phase to the oil phase slowly with constant stirring at high speed (creating a vortex). Continue stirring for 5 minutes.
4. Homogenise the product for 5 minutes at 3500 rpm using a Silverson mixer or equivalent.

Composition 2—Representative Oil-In-Water Emulsion Cosmetic Composition

| Material | % w/w |
| --- | --- |
| Dimethicone | 5.50 |
| Water | 79.95 |
| Glycerin | 5.00 |
| Dimethicone crosspolymer & Dimethicone | 1.00 |
| Phenoxyethanol & Methylparaben & Ethylparaben | 0.80 |
| Glyceryl stearate & PEG-100 stearate | 2.00 |
| Cetearyl alcohol | 2.00 |
| Sodium polyacrylate | 0.60 |
| Xanthan gum | 0.10 |

-continued

| Material | % w/w |
| --- | --- |
| Tetrasodium EDTA | 0.05 |
| Peptide excipient composition comprising propanediol & Pentylene glycol & Decyl glucoside & Water excipient composition | 3.00 |

Method of Manufacture

1. To water add glycerine and dissolve tetrasodium EDTA.
2. Using homogenisation sprinkle in xanthan gum and continue to homogenise for 5 minutes or until hydrated.
3. Heat water phase to 70-75° C.
4. In a separate vessel weigh out oil phase and heat to 70-75° C. (Dimethicone, cetearyl alcohol, glyceryl stearate & PEG-100 stearate) When at temperature stir in the sodium polyacrylate.
5. With both phases at 70-75° C. add the oil phase to the water phase and homogenise for 2 minutes.
6. Add dimethicone crosspolymer & dimethicone and homogenise for 2 minutes.
7. Cool to room temperature.
8. Stir in phenoxyethanol & methylparaben & ethylparaben and peptide & propanediol & pentylene glycol & decyl glucoside & water.
9. Make to weight with water and stir smooth.

Composition 3—Representative Gel-Based Cosmetic Composition

| Material | % w/w |
| --- | --- |
| Glycerin | 5.00 |
| Propanediol | 2.00 |
| Acrylates/C10-30 alkyl acrylate crosspolymer | 1.00 |
| Alcohol denat. | 0.50 |
| Phenoxyethanol & Methylparaben & Ethylparaben | 0.40 |
| Potassium hydroxide | 0.29 |
| Tetrasodium EDTA | 0.05 |
| Peptide excipient composition comprising propanediol & Pentylene glycol & Decyl glucoside & Water excipient composition | 3.00 |
| Water | 87.76 |

Method of Manufacture

1. To water add glycerine and propanediol and dissolve tetrasodium EDTA.
2. Using homogenisation sprinkle in acrylates/C10-30 alkyl acrylate crosspolymer and continue to homogenise for 5 minutes or until hydrated.
3. Stir in potassium hydroxide to form gel.
4. Stir in alcohol denat., phenoxyethanol & methylparaben & ethylparaben and peptide & propanediol & pentylene glycol & decyl glucoside & water.
5. Make to weight with water and stir smooth.

The invention claimed is:

1. A tetrapeptide, capable of inducing dermal extracellular matrix protein upregulation, selected from the group consisting of tetrapeptides having the amino acid sequence

U-QTAV-Z wherein QTAV is SEQ ID NO: 1 and Q is used to denote a Glutamine residue, T is used to denote a Threonine residue, A is used to denote an Alanine residue, and V is used to denote a Valine residue, wherein at the N-terminal end, U is independently selected from the group consisting of octanoyl (C8), decanoyl (C10), lauroyl (C12), myristoyl (C14), palmitoyl (C16), stearoyl (C18), biotinoyl, elaidoyl, oleoyl, and lipoyl, wherein at the C-terminal end, Z is selected from the group consisting of OH, $OR^1$, $NHR^1$, or $NR^1R^2$, wherein $R^1$ and $R^2$ are independently selected from the group consisting of alkyl, aryl, aralkyl, alkylaryl, alkoxy, saccharide, and aryloxy groups, which may be linear, branched, cyclical, polycyclic, unsaturated, hydroxylates, carbonylated, phosphorylated, and/or sulphurous, said $R^1$ and $R^2$ groups comprising from 1 to 24 carbon atoms and being capable of including one or more heteroatoms O, S, and/or N.

2. A tetrapeptide according to claim 1 wherein U of the tetrapeptide is independently selected from the group consisting of lauroyl (C12), myristoyl (C14) and palmitoyl (C16).

3. A cosmetic composition comprising the tetrapeptide of claim 1.

4. A cosmetic composition according to claim 3 wherein the tetrapeptide is present from 0.1 to 10,000 ppm by weight of the composition.

5. A cosmetic composition according to claim 4 further comprising additional further peptides selected from the group consisting of dipeptides, tripeptides, additional tetrapeptides, pentapeptides and mixtures thereof.

6. A method for stimulating the production of dermal extracellular proteins in humans, the method comprising administering to the skin of said human a cosmetically effective amount of a tetrapeptide according to claim 1.

* * * * *

SEQUENCE LISTING

```
<160> NUMBER OF SEQ ID NOS: 17

<210> SEQ ID NO 1
<211> LENGTH: 4
<212> TYPE: PRT
<213> ORGANISM: Homo sapiens

<400> SEQUENCE: 1
```

-continued

```
Gln Thr Ala Val
1

<210> SEQ ID NO 2
<211> LENGTH: 5
<212> TYPE: PRT
<213> ORGANISM: Homo sapiens

<400> SEQUENCE: 2

Lys Lys Thr Lys Ser
1               5

<210> SEQ ID NO 3
<211> LENGTH: 4
<212> TYPE: PRT
<213> ORGANISM: Homo sapiens

<400> SEQUENCE: 3

Gly Gln Pro Arg
1

<210> SEQ ID NO 4
<211> LENGTH: 4
<212> TYPE: PRT
<213> ORGANISM: Homo sapiens

<400> SEQUENCE: 4

Glu Gln Pro Arg
1

<210> SEQ ID NO 5
<211> LENGTH: 4
<212> TYPE: PRT
<213> ORGANISM: Homo sapiens

<400> SEQUENCE: 5

Ala Gln Thr Arg
1

<210> SEQ ID NO 6
<211> LENGTH: 4
<212> TYPE: PRT
<213> ORGANISM: Homo sapiens
<220> FEATURE:
<223> OTHER INFORMATION: Xaa at position 1 is Gly or the amino acids
      that may be substituted therefore, Xaa at position 2 is Gln or the
      amino acids that may be substituted therefore and Xaa at position
      4 may be Pro or Arg or the amino acids substituted therefore

<400> SEQUENCE: 6

Xaa Xaa Arg Xaa
1

<210> SEQ ID NO 7
<211> LENGTH: 4
<212> TYPE: PRT
<213> ORGANISM: Homo sapiens
<220> FEATURE:
<223> OTHER INFORMATION: Xaa at position 1 is Gly or the amino acids
      that may be substituted therefore, Xaa at position 2 is Gln or the
      amino acids that may be substituted therefore and Xaa at position
      3 may be Pro or Arg or the amino acids substituted therefore

<400> SEQUENCE: 7

Xaa Xaa Xaa Pro
1
```

```
<210> SEQ ID NO 8
<211> LENGTH: 4
<212> TYPE: PRT
<213> ORGANISM: Homo sapiens
<220> FEATURE:
<223> OTHER INFORMATION: Xaa at position 1 is Gly or the amino acids
      that may be substituted therefore and Xaa at position 2 is Gln or
      the amino acids that may be substituted therefore

<400> SEQUENCE: 8

Xaa Xaa Pro Arg
1

<210> SEQ ID NO 9
<211> LENGTH: 4
<212> TYPE: PRT
<213> ORGANISM: Homo sapiens
<220> FEATURE:
<223> OTHER INFORMATION: Xaa at position 1 is Gly or the amino acids
      that may be substituted therefore, Xaa at position 2 is Gln or the
      amino acids that may be substituted therefore and Xaa at position
      4 may be Pro or Arg or the amino acids substituted therefore

<400> SEQUENCE: 9

Xaa Xaa Pro Xaa
1

<210> SEQ ID NO 10
<211> LENGTH: 4
<212> TYPE: PRT
<213> ORGANISM: Homo sapiens
<220> FEATURE:
<223> OTHER INFORMATION: Xaa at position 1 is Gly or the amino acids
      that may be substituted therefore, Xaa at position 2 is Gln or the
      amino acids that may be substituted therefore and Xaa at position
      3 may be Pro or Arg or the amino acids substituted therefore

<400> SEQUENCE: 10

Xaa Xaa Xaa Arg
1

<210> SEQ ID NO 11
<211> LENGTH: 4
<212> TYPE: PRT
<213> ORGANISM: Homo sapiens

<400> SEQUENCE: 11

Arg Ser Arg Lys
1

<210> SEQ ID NO 12
<211> LENGTH: 5
<212> TYPE: PRT
<213> ORGANISM: Homo sapiens

<400> SEQUENCE: 12

Lys Thr Thr Lys Ser
1               5

<210> SEQ ID NO 13
<211> LENGTH: 5
<212> TYPE: PRT
<213> ORGANISM: Homo sapiens

<400> SEQUENCE: 13

Arg Asp Lys Tyr Val
1               5
```

```
<210> SEQ ID NO 14
<211> LENGTH: 4
<212> TYPE: PRT
<213> ORGANISM: Homo sapiens

<400> SEQUENCE: 14

Gly Tyr Ile Leu
1

<210> SEQ ID NO 15
<211> LENGTH: 4
<212> TYPE: PRT
<213> ORGANISM: Homo sapiens

<400> SEQUENCE: 15

Leu Ser Pro Gly
1

<210> SEQ ID NO 16
<211> LENGTH: 4
<212> TYPE: PRT
<213> ORGANISM: Homo sapiens

<400> SEQUENCE: 16

Gly Pro Ser Gly
1

<210> SEQ ID NO 17
<211> LENGTH: 4
<212> TYPE: PRT
<213> ORGANISM: Homo sapiens

<400> SEQUENCE: 17

Leu Ser Pro Asp
1
```